US010881874B2

(12) United States Patent
Tarlano

(10) Patent No.: US 10,881,874 B2
(45) Date of Patent: Jan. 5, 2021

(54) RADIATION SOURCE FOR CANCER TREATMENT

(71) Applicant: John P. Tarlano, Fayetteville, GA (US)

(72) Inventor: John P. Tarlano, Fayetteville, GA (US)

( * ) Notice: Subject to any disclaimer, the term of this patent is extended or adjusted under 35 U.S.C. 154(b) by 87 days.

(21) Appl. No.: 16/350,773

(22) Filed: Dec. 31, 2018

(65) Prior Publication Data
US 2020/0206530 A1 Jul. 2, 2020

(51) Int. Cl.
*A61N 5/10* (2006.01)
*A61P 35/00* (2006.01)
*A61N 5/06* (2006.01)

(52) U.S. Cl.
CPC ............... *A61N 5/10* (2013.01); *A61P 35/00* (2018.01); *A61N 2005/0627* (2013.01); *A61N 2005/1019* (2013.01)

(58) Field of Classification Search
CPC .............. A61N 5/10; A61N 2005/0627; A61N 2005/1019; A61P 35/00
See application file for complete search history.

(56) References Cited

U.S. PATENT DOCUMENTS

| | | | | |
|---|---|---|---|---|
| 6,241,651 B1* | 6/2001 | Smith | ............... | A61N 5/1001 600/1 |
| 6,975,702 B2* | 12/2005 | Tarlano | ............... | A61N 5/10 378/65 |
| 7,308,078 B2* | 12/2007 | Wilkins | ............... | H01J 35/08 378/124 |
| 7,949,101 B2* | 5/2011 | Morton | ............... | G01V 5/00 378/124 |
| 2009/0136001 A1* | 5/2009 | DeSalvo | ............... | H01J 35/16 378/124 |

OTHER PUBLICATIONS

Adjei et al., DNA strand breaks induced by soft x-ray pulses from a compact laser plasma source, Nov. 26, 2015, Radiation Physics and Chemistry, vol. 120, pp. 17-25. (Year: 2015).*
Farshad et al., A Retrospective study of 150 patients with lentigo maligna and lentigo maligna melanoma and the efficacy of radiotherapy using Grenz or soft x-rays, 2002, British Journal of Dematology, vol. 146, pp. 1042-1046. (Year: 2002).*
Sato et al., A laser plasma produced soft x-ray laser at 89 eV generates DNA double strand breaks in human cancer cells., 2015, Journal of Radiation Research, vol. 56, pp. 633-638. (Year: 2015).*

* cited by examiner

*Primary Examiner* — Christine S. Kim

(57) ABSTRACT

A radiation source that simultaneously produces two radiation frequencies of combined radiation, in order to break apart a mutated DNA base pair. The radiation source produces combined radiation, the combined radiation being for a thymine base and a cytosine base in a thymine and cytosine base pair. The radiation source produces combined radiation, the combined radiation being for a guanine base and a thymine base in a guanine and thymine base pair. The radiation source produces combined radiation, the combined radiation being for an adonine base and a guanine base in an adonine and guanine base pair. The radiation source produces combined radiation, the combined radiation being for an adonine base and a cytosine base in an adonine and cytosine base pair.

1 Claim, 1 Drawing Sheet

RADIATION SOURCE FOR CANCER TREATMENT

A soft x-ray source for targeting a DNA mutation of a cancer cell, for cancer cell inactivation, is disclosed. Two soft x-ray beams are simultaneously emitted from the soft x-ray source.

An anode of a soft-x-ray radiation source, including an anode of a soft x-ray tube, is plated with a first and a second metal. The first metal is a source of approximately 500 electron-volt soft x-ray radiation, that is 500 ev radiation, in a combined soft x-ray beam. The second metal is the source of approximately 400 electron-volt soft x-ray radiation in the combined soft x-ray beam.

The soft x-ray source produces a combined soft x-ray beam, the combined soft x-ray beam containing two radiation frequencies, the two radiation frequencies corresponding to approximately 500 ev and approximately 400 ev. The two radiation frequencies are in the soft x-ray region.

The approximately 500 ev soft x-ray radiation energizes a Guanine base of a mutated Guanine-Thymine base pair or a mutated Guanine-Adonine base pair of a cancer cell. The approximately 500 ev soft x-ray radiation energizes a Cytosine base of a mutated Cytosine-Thymine base pair or mutated Cytosine-Adonine base pair of a cancer cell.

The approximately 400 ev soft x-ray radiation energizes a Thymine base of a mutated Guanine-Thymine base pair or a Thymine base of a mutated Thymine-Cytosine base pair. The approximately 400 ev soft x-ray radiation energizes the Adonine base of a mutated Adonine-Guanine base pair or mutated Adonine-Cytosine base pair of a cancer cell.

The approximately 400 ev beam and approximately 500 ev beam in a combined soft x-ray beam breaks apart the two DNA bases of a mutated DNA base pair of a cancer cell, and causes cell inactivation.

The mutated DNA base pair is due to a mutation of a normal DNA base pair of a normal cell. There are four different mutated DNA base pairs: T-G, T-C, A-G, and A-C, of a cancer cell.

For mutated DNA base pair T-G, the two radiation frequencies of the combined beam are 383 ev and 528 ev.

For mutated DNA base pair T-C, the two radiation frequencies of the combined beam are 383 ev and 528 ev.

For mutated DNA base pair A-G, the two radiation frequencies of the combined beam are 392 ev and 528 ev.

For mutated DNA base pair A-C, the two radiation frequencies of the combined beam are 392 ev and 528 ev.

The penetration depth in skin is 10 microns for 400 ev radiation and is 100 microns for 600 ev radiation. The penetration depth is almost linear between 400 ev and 600 ev.

As is known in the art, T stands for a T base of DNA, which is Thymine. C stands for a C base of DNA, which is Cytosine. A stands for an A base of DNA, which is Adonine. G stands for a G base of DNA, which is Guanine.

The teaching of U.S. Pat. No. 6,975,702, issued on Dec. 13, 2005, are incorporated herein by reference.

DESCRIPTION OF THE PREFERRED EMBODIMENT

Figure 1:
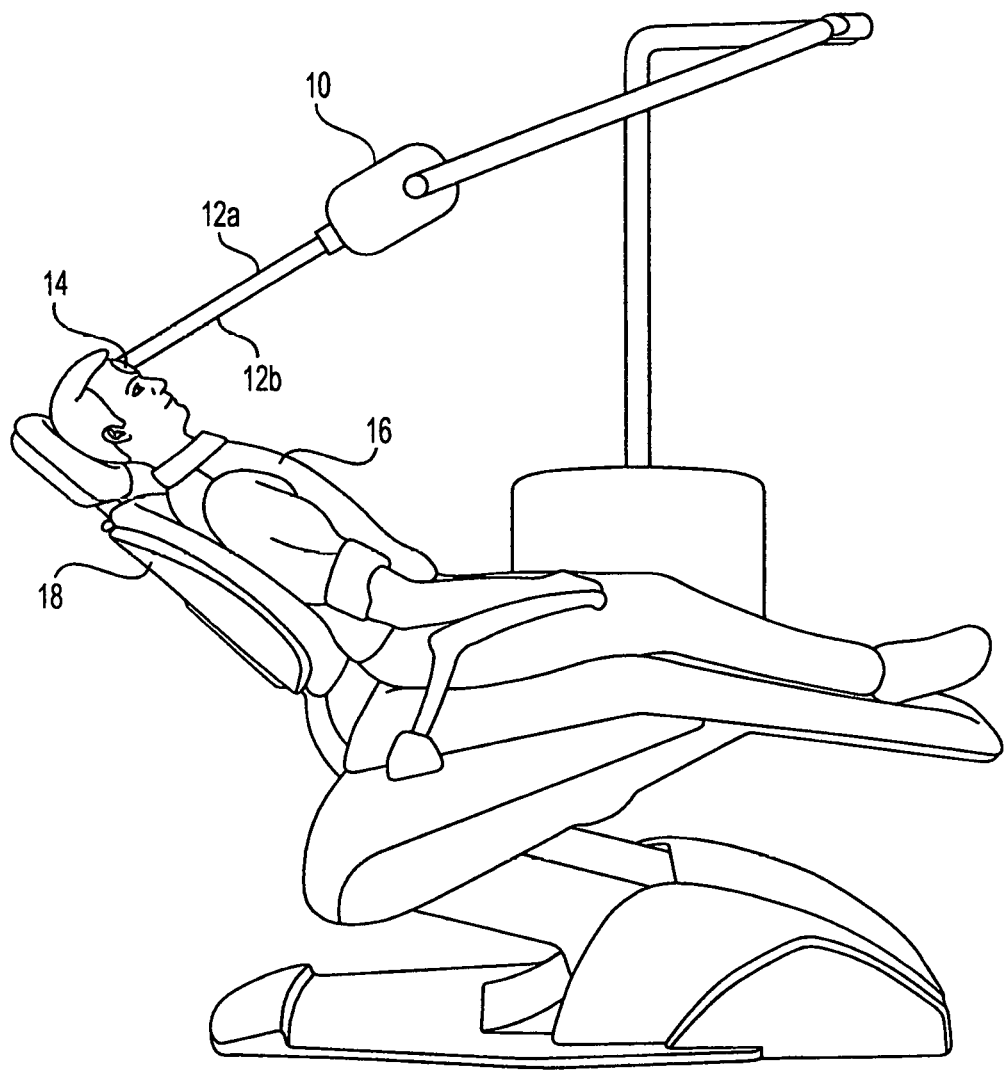
FIG. 1 shows one beam that has two soft x-ray frequencies, for targeting a cancer spot on a person.
Figure 2:
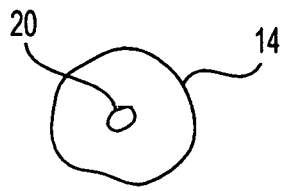
FIG. 2 shows a cancer spot and cancer cells in the cancer spot.

In FIG. 1, a soft x-ray source 10 sends a soft x-ray beams 12a and 12b into a cancer spot 14 that is located in the skin of a cancer patient 16. Cancer spot 14 is shown in FIGS. 1 and 2. In FIG. 2, cancer cells 20 are located in cancer spot 14.

Cancer patient 16 rests in a chair 18. Chair 18 holds soft x-ray source 10.

Figure 3:
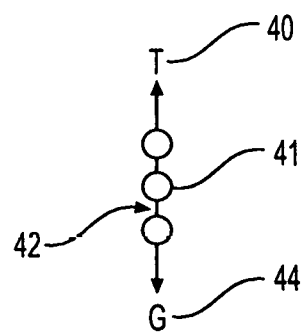
FIG. 3 shows a mutation due to Thymine base being coupled a Guanine base.

Soft x-ray source 10 sends a soft x-ray beams 12a and 12b into a mutation 42, shown in FIG. 3, in cancer cells 20

Soft x-ray radiation in beam 12a has energy of approximately 383 ev, and has an associated frequency. The 383 ev radiation in beam 12a originates from a first metal on a first and second metal coated anode of soft x-ray source 10. The soft x-ray source 10 may be an x-ray tube.

The soft x-ray radiation of beam 12a targets the Thymine, T, DNA base 40 of a T-G DNA base pair of mutation 42, shown in FIG. 3. Mutation 42 is in cancer cells 20 in cancer spot 14, shown in FIG. 2.

Simultaneously, x-ray source 10 sends soft x-ray beam 12b into G DNA base 44 of mutation 42 in cancer cells 20. Soft x-ray radiation 12b has energy of approximately 528 ev and has an associated frequency.

The soft x-ray radiation in beam 12b originates from a second metal on a first and second metal coated anode of soft x-ray source 10. The second metal radiation of beam 12b targets the Guanine, G, DNA base 44 of T-G mutation 42, shown in FIG. 3. Again mutation 42 is in cancer cells 20 in cancer spot 14.

The soft x-ray beams 12a and 12b target the DNA T base 40 and DNA G base 44 simultaneously. The soft x-rays of beams 12a and 12b break apart the bonds between electrons 41 between base T and base G, shown in FIG. 3. The base T and base G of mutation 42 are broken apart by the joint action of the titanium radiation and nickel radiation of soft x-rays in beams 12a and 12b. Cancer cells 20 are inactivated.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A radiation source comprising an anode, the anode having a first metal of a first metal plating and a second metal of a separate second metal plating, the first metal for producing a 383 ev soft x-ray beam for targeting either a Thymine base or Adenine base of a DNA base pair mutation, and the second metal for producing a 528 ev soft x-ray beam for targeting either a Guanine base or a Cytosine base of the DNA base pair mutation, the productions being simultaneous.

* * * * *